(12) United States Patent
Macduff

(10) Patent No.: US 9,855,148 B2
(45) Date of Patent: Jan. 2, 2018

(54) SKELETAL REPLACEMENT SYSTEM AND METHOD OF USE THEREOF

(71) Applicant: Charles Colin Macduff, Olympia, WA (US)

(72) Inventor: Charles Colin Macduff, Olympia, WA (US)

( * ) Notice: Subject to any disclaimer, the term of this patent is extended or adjusted under 35 U.S.C. 154(b) by 45 days.

(21) Appl. No.: 15/051,643

(22) Filed: Feb. 23, 2016

(65) Prior Publication Data

US 2016/0242911 A1      Aug. 25, 2016

Related U.S. Application Data

(60) Provisional application No. 62/119,710, filed on Feb. 23, 2015.

(51) Int. Cl.
*A61F 2/30*    (2006.01)
*A61F 2/42*    (2006.01)
*A61F 2/28*    (2006.01)

(52) U.S. Cl.
CPC .......... *A61F 2/4241* (2013.01); *A61F 2/4225* (2013.01); *A61F 2/28* (2013.01); *A61F 2002/3096* (2013.01); *A61F 2002/30331* (2013.01); *A61F 2002/30604* (2013.01); *A61F 2002/30624* (2013.01); *A61F 2002/30637* (2013.01); *A61F 2002/4246* (2013.01); *A61F 2002/4248* (2013.01); *A61F 2310/00179* (2013.01)

(58) Field of Classification Search
CPC .... A61F 2/4225; A61F 2/4241; A61F 2/3804; A61F 2002/30331; A61F 2002/30624; A61F 2002/30637; A61F 2002/4228; A61F 2002/423; A61F 2002/4233; A61F 2002/4235; A61F 2002/4238; A61F 2002/4243; A61F 2002/4246; A61F 2002/4248; A61F 2002/4251
See application file for complete search history.

(56) References Cited

U.S. PATENT DOCUMENTS 5,984,970 A * 11/1999 Bramlet ............. A61B 17/1659
                                                        623/21.15
2014/0114428 A1* 4/2014 Weems ................. A61F 2/4241
                                                        623/21.15

* cited by examiner

*Primary Examiner* — Brian Dukert

(57) ABSTRACT

A skeletal replacement system may be utilized to replace bones in a patient. The skeletal replacement system has least one skeletal replacement linkage, each skeletal replacement linkage having a first member, a second member, and a hinge. The first and second members are hingedly coupled by the hinge. Multiple skeletal replacement linkages may be coupled end to end through a shaft on the second member of a first linkage being inserted into a bore in the first member of a second linkage. Each linkage is configured to replace at least a portion of each of two bones and a joint in a patient's body. Multiple linkages may be used to replace more bones and joints as required.

13 Claims, 6 Drawing Sheets

SKELETAL REPLACEMENT SYSTEM AND METHOD OF USE THEREOF

The current application claims a priority to the U.S. Provisional Patent application Ser. No. 62/119,710 filed on Feb. 23, 2015.

FIELD OF THE INVENTION

The present invention relates generally to osteology. More particularly, the present invention relates to bone repair.

BACKGROUND OF THE INVENTION

Some bodily injuries cause damage that is difficult to heal or repair. For example, injuries to the bones in fingers and toes can be difficult for medical professionals to treat. In some instances, medical professionals may be able to reset damaged bones in fingers and toes. However, in such circumstances, fingers and toes often heal with bends or curves which can be irritating or painful for patients for the rest of their lives. As an alternative to resetting damaged bones, medical professionals may amputate some or all of fingers and toes. Amputation causes permanent physical deformity, but may be a favorable outcome compared with the irritation and/or pain from reset damaged bones.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced without the implementation of some features as they are described. It should be understood that some details have not been described in detail in order to not unnecessarily obscure focus of the invention.

Figure 1:
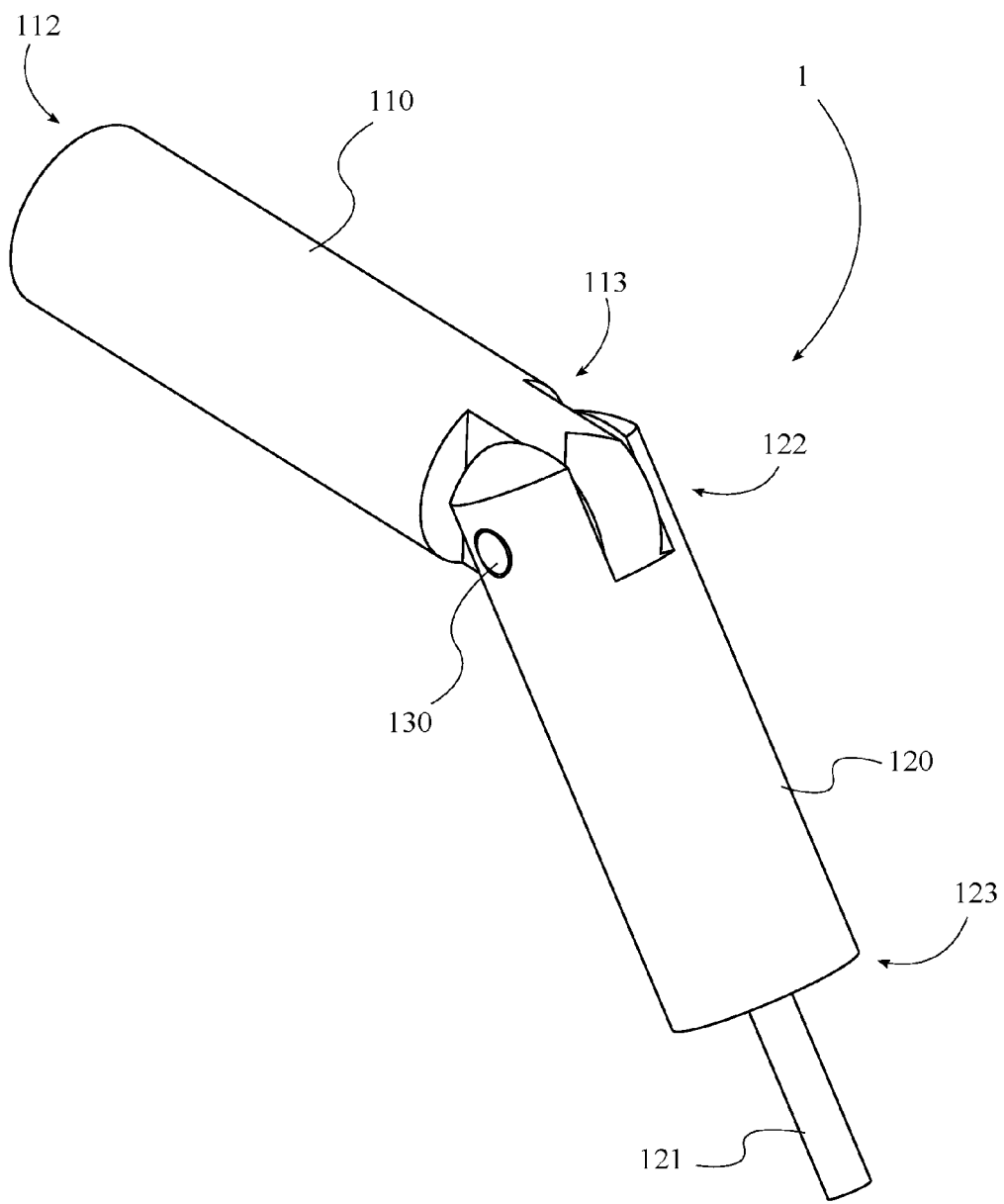
FIG. 1 is a perspective view of an embodiment of a skeletal replacement linkage.
Figure 2:
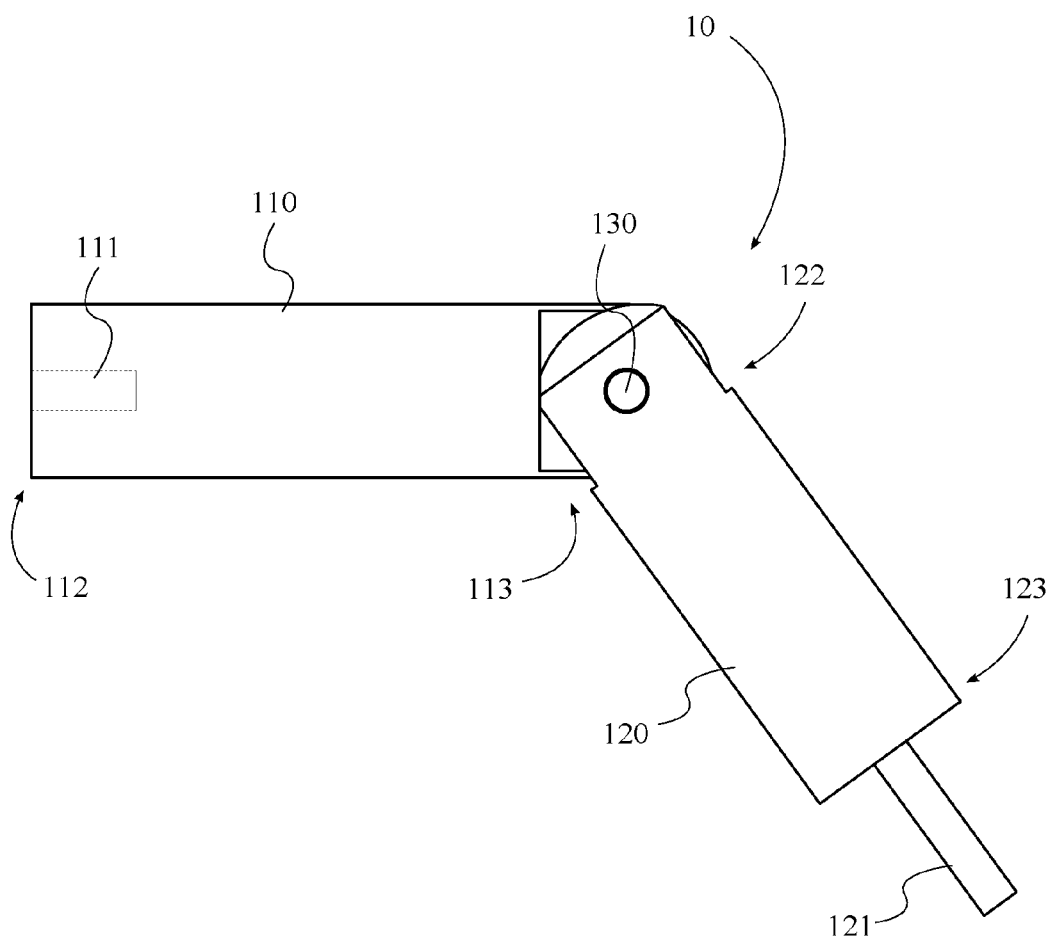
FIG. 2 is a side view of an embodiment of a skeletal replacement linkage.
Figure 3:
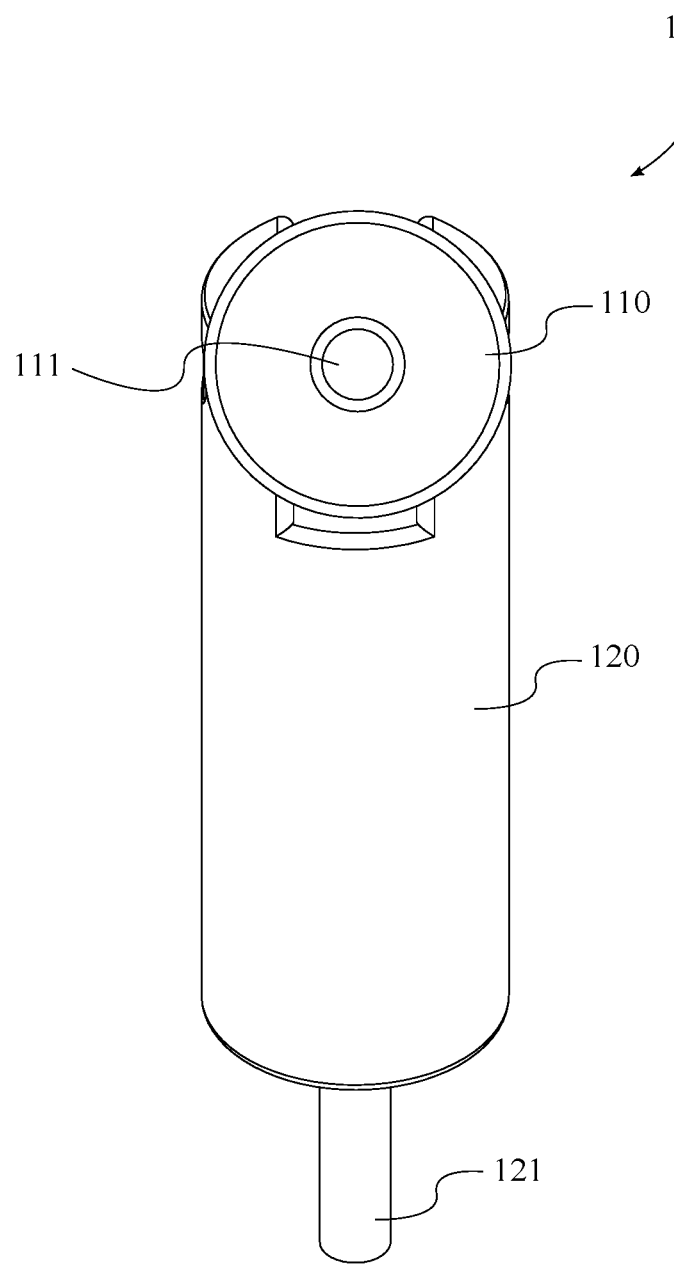
FIG. 3 is a rear view of an embodiment of a skeletal replacement linkage.

The present invention is a skeletal replacement system 1 utilizing linkages of members intended and configured for use in treatment, repair or replacement of bones in a human patient. Referring to FIGS. 1-3, the present invention generally comprises at least one skeletal replacement linkage 10. Each of the at least one skeletal replacement linkage 10 comprises a first member 110, a second member 120, and a hinge 130. Each of the skeletal replacement linkages 10 are coupled in series with each other, or alternatively stated, the skeletal replacement linkages 10 are connected end to end.

The first member 110 comprises a bore 111, a first end 112 and a second end 113. The second member 120 comprises a shaft 121, a first end 122 and a second end 123. The bore 111 of the first member 110 traverses into the first end 112 of the first member 110 opposite the hinge 130. The shaft 121 of the second member 120 extends from the second end 123 of the second member 120 opposite the hinge 130. The second end 113 of the first member 110 and the first end 122 of the second member 120 are hingedly coupled to each other by the hinge 130. In the preferred embodiment of the present invention, the diameter of the bore 111 is selected such that the shaft 121 of another skeletal replacement linkage 10 can be inserted into the bore 111. Additionally in the preferred embodiment, a diameter of the shaft 121 is selected such that the shaft 121 can be inserted into a bore 111 of another skeletal replacement linkage 10. In one embodiment, the bore 111 is concentrically positioned within the first member 110. Additionally, the shaft 121 is concentrically positioned on the second member 120. However it should be noted that the bore 111 and the shaft 121 may be positioned laterally off-center with their respective members if necessary or desired.

In one embodiment, the first member 110 and the second member 120 are comprised of non-metallic materials, such as a plastic or ceramic. For example, one form of plastic includes plastic created by three dimensional rapid prototyping machines. Furthermore, in one embodiment, the non-metallic materials comprise one or more of medical grade plastic or medical grade ceramic. In one embodiment, the first member 110 and the second member 120 have rigidity, compression strength, and tensile strength equal to or greater than human bones. In one embodiment, the hinge 130 includes a rod, such as a rod made from stainless steel, surgical steel, or titanium.

In a first specified embodiment, the at least one skeletal replacement linkage 10 comprises only a single skeletal replacement linkage 10. In the first specified embodiment, the single skeletal replacement linkage 10 is configured to replace at least a portion of each of two bones and a joint in a patient's body. FIGS. 1-3 show the first specified embodiment.

In various embodiments, the at least one skeletal replacement linkage 10 comprises two or more skeletal replacement linkages 10. More particularly, in a second specified embodiment shown in FIGS. 4-6, the at least one skeletal replacement linkage 10 comprises a first skeletal replacement linkage 100 and a second skeletal replacement linkage 101. The second specified embodiment is configured to replace at least a portion of a first bone, a second bone, at least a portion of a third bone, a first joint between the first and second bones, and a second joint between the second and third bones in the patient's body.

In the second specified embodiment, the shaft 121 of the second member 120 of the first skeletal replacement linkage 100 is inserted within the bore 111 of the first member 110 of the second skeletal replacement linkage 101, coupling the first skeletal replacement linkage 100 and the second skeletal replacement linkage 101 together. Thus, in one embodiment, the shaft 121 of the second member 120 of the first skeletal replacement linkage 100 may be adhered to the bore 111 of the first member 110 of the second skeletal replacement linkage 101, or the shaft 121 of the second member 120 of the first skeletal replacement linkage 100 may be press fit into the bore 111 of the first member 110 of the second skeletal replacement linkage 101, or other means may be utilized to connect the second member 120 of the first skeletal replacement linkage 100 into the bore 111 of the first member 110 of the second skeletal replacement linkage 101 in other embodiments.

The skeletal replacement linkage 10 can be used to replace bones in a human body. In the general method of use of the skeletal replacement system 1, a first bone of a patient is prepared to receive the shaft 121 of the second member 120 of one of the skeletal replacement linkages 10. The second member 120 of the skeletal replacement linkage 10 is trimmed based on an intended distance from the prepared first bone to an intended location of the hinge 130. The shaft 121 is inserted into the prepared first bone, and tissue is placed around the skeletal replacement system 1. A second bone may also be removed from the patient, wherein the first member 110, the hinge 130, and the second member 120 of the skeletal replacement linkage 10 are configured to replace, respectively the second bone, a joint between the second bone and the first bone, and a portion of the first bone. The tissue may be placed around the skeletal replacement linkage 10 by physically replacing the patient's tissue around the skeletal replacement linkage 10 with tissue from another body part of the patient or donor tissue, or the tissue may be regrown around the skeletal replacement linkage 10 using a stem cell technique, or the tissue may be grown around the skeletal replacement linkage 10 before inserting the shaft 121 of the skeletal replacement linkage 10 into the prepared first bone.

The following description uses an example of skeletal replacement linkage 10 replacing bones in a finger; however, the skeletal replacement linkage 10 can be used in other situations, such as to replace bones in thumbs, toes, arms, legs, and the like. In one example, a patient suffered damage to the middle phalange and/or distal interphalangeal (DIP) joint of a finger. Rather than amputating the finger and/or resetting the damaged bones, a medical professional may remove the distal phalange of the finger and cut off the damaged portion of the middle phalange. The medical professional can drill a bore 111 in the remaining portion of the middle phalange to receive the shaft 121 of the skeletal replacement linkage 10. Once the shaft 121 of the skeletal replacement linkage 10 is inserted into the bore 111 in the remaining portion of the middle phalange, the second member 120, the hinge 130, and the first member 110 serve to replace, respectively, the damaged portion of the middle phalange, the DIP joint, and the distal phalange. The medical professional can then restore the soft tissue of the patient's finger around the skeletal replacement linkage 10 and close the skin of the patient's finger.

The length that the second member 120 needs to be in the patient's finger depends on a number of factors, such as the original length of the patient's middle phalange before it was injured, the length of the undamaged portion of the middle phalange, and/or the size of the patient's DIP joint. To allow for different lengths of the second member 120, the second member 120, in one embodiment, is made from a material that can be trimmed by the medical professional prior to placement of the skeletal replacement linkage 10 in the patient's finger. For example, the second member 120 can be made of plastic that can be trimmed to the correct length with instruments available to the medical professional, such as a scalpel. In this way, the medical professional may trim the second member 120 to the appropriate length as part of the procedure to insert the skeletal replacement linkage 10 into the patient's finger. The medical professional may determine the appropriate length based on X-rays of the patient's finger before the injury, based on a size of the corresponding finger on the patient's uninjured hand, or in any other way. Similarly, the length of the shaft 121 can be determined and, if needed, trimmed prior to insertion of the skeletal replacement linkage 10 in the patient's finger.

Once placed into a patient's finger, the skeletal replacement linkage 10 provides structural stability that was previously provided by the patient's bones. In addition for providing structural stability, the skeletal replacement linkage 10 also provides structure for the regrowing of soft tissue in the finger. Medical research has developed techniques for regrowing various tissues, such as skin, tendon, and fingernail tissues. In one example, scientists have developed a powder made from pig bladder tissue that stimulates stem cell growth to regrow lost tissue. The skeletal replacement linkage 10 can provide structure for the other tissues of the finger, such as skin, tendon, and fingernail tissues, to be regrown using stem cell techniques, such as powder made from pig bladder. In one embodiment, with a fresh wound, the skeletal replacement linkage 10 can be placed in the patient's finger even if some or most of the patient's soft tissue no longer remains attached to the finger and stem cell techniques can be used to promote regeneration of the lost tissue around the skeletal replacement linkage 10. In another embodiment, even after time has passed since an amputation that left a finger stub, the finger stub can be reopened to have the skeletal replacement linkage 10 attached and then stem cell techniques can be used to grow tissue around the skeletal replacement linkage 10. In yet another embodiment, even after time has passed since an amputation that left a finger stub, stem cell techniques can be used to grow tissue around the skeletal replacement linkage 10 and then the finger stub can be reopened to have the skeletal replacement linkage 10 attached with the regrown tissue already on the skeletal replacement linkage 10.

The second specified embodiment of the skeletal replacement system 1 comprising a first skeletal replacement linkage 100 and a second skeletal replacement linkage 101 can be used to replace bones and two joints, such as replacing a distal phalange, a DIP joint, a middle phalange, a proximal interphalangeal (PIP) joint, and a portion of a proximal phalange. In this case, once the bore 111 of the second member 120 of the second skeletal replacement linkage 101 is inserted into a bore 111 of a remaining portion of the proximal phalange, the second member 120 of the second skeletal replacement linkage 101, the hinge 130 of the second skeletal replacement linkage 101, the combination of the first member 110 of the second skeletal replacement linkage 101 and the second member 120 of the first skeletal replacement linkage 100, the hinge 130 of the first skeletal replacement linkage 100, and the first member 110 of the first skeletal replacement linkage 100 serve to replace, respectively, the damaged portion of the proximal phalange, the PIP joint, the middle phalange, the DIP joint, and the distal phalange. The shafts 121 of the first skeletal replacement linkage 100 and of the second skeletal replacement linkage 101 can be held, respectively, to the bore 111 of the second skeletal replacement linkage 101 and the bore 111 in the remaining portion of the proximal phalange using a medical grade adhesive or any other appropriate adhesive. Alternatively, the shaft 121 of the first skeletal replacement linkage 100 and the bore 111 of the second skeletal replacement linkage 101 may be designed with a press fit such that the shaft 121 of the first skeletal replacement linkage 100 will not easily be removed from the bore 111 of the second skeletal replacement linkage 101 after it has been inserted into the bore 111 of the second skeletal replacement linkage 101.

The lengths of the various linkages in the skeletal replacement system 1 can be modified to fit the proper lengths of the patient's finger. For example, the first member 110 of the first skeletal replacement linkage 100 can be trimmed to provide the proper length of the patient's distal bone. In another example, one or both of the second member 120 of the first skeletal replacement linkage 100 and the first member 110 of the second skeletal replacement linkage 101 can be trimmed such that the distance between the hinge 130 of the first skeletal replacement linkage 100 and the hinge 130 of the second skeletal replacement linkage 101 is the same as the distance between the patient's DIP and PIP joints. In another example, the second member 120 of the second skeletal replacement linkage 101 is trimmed such that the hinge 130 of the second skeletal replacement linkage 101 is located in the former position of the PIP joint when the shaft 121 of the second skeletal replacement linkage 101 is inserted into the bore 111 in the undamaged portion of the proximal phalange.

Figure 4:
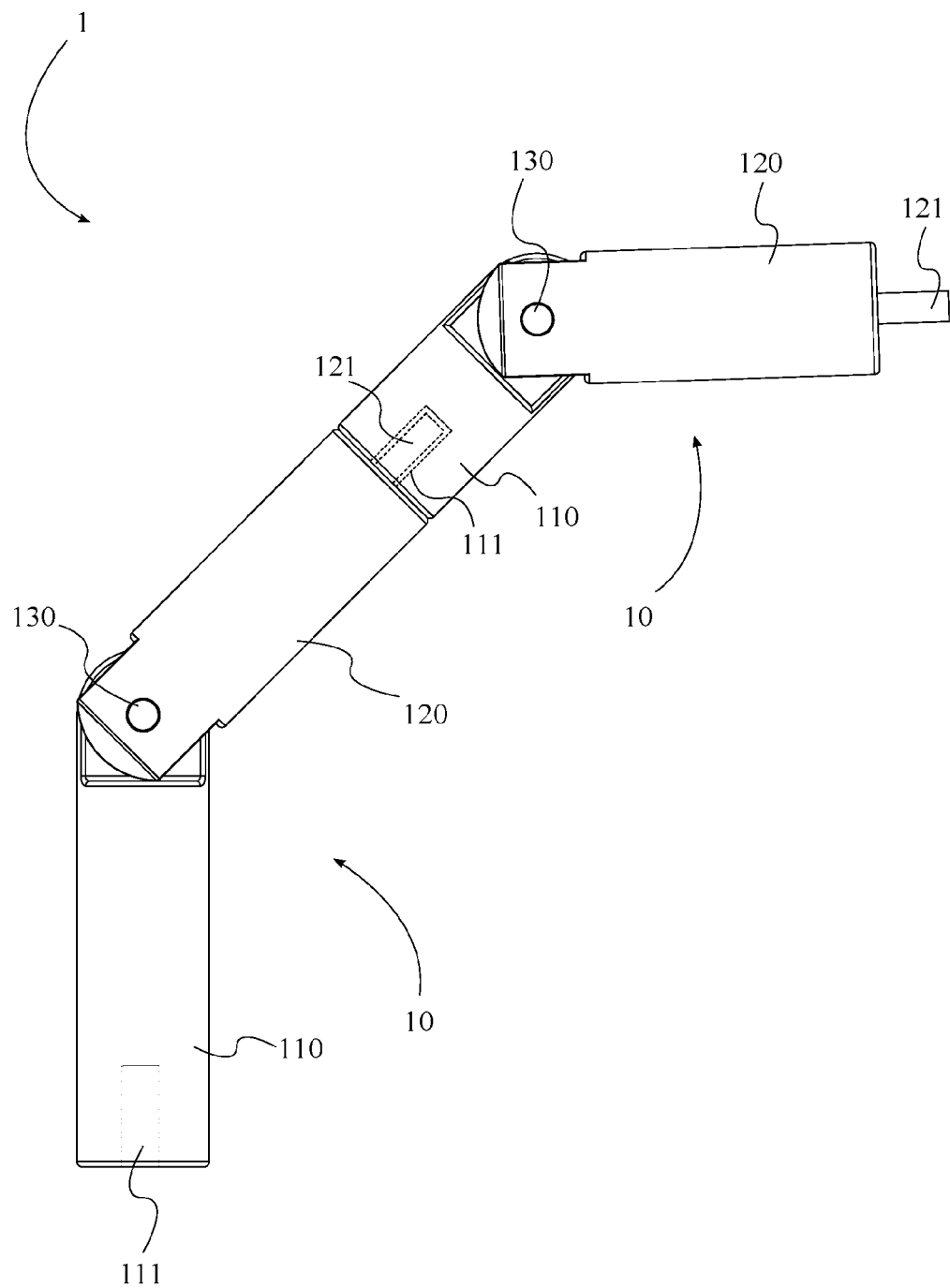
FIG. 4 is a side view of an embodiment of the skeletal replacement system with two skeletal replacement linkages.
Figure 5:
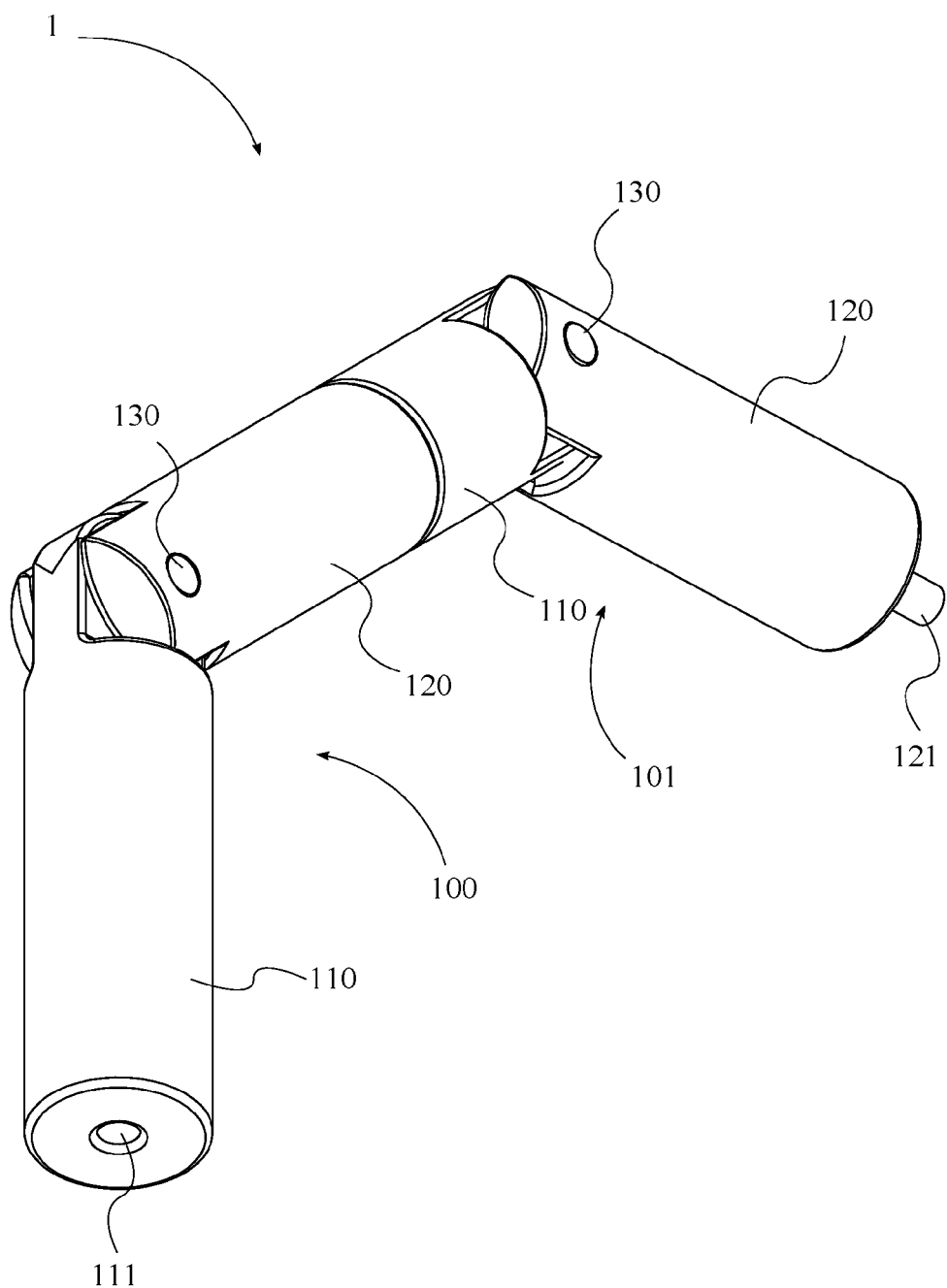
FIG. 5 is a lowered perspective view of an embodiment of the skeletal replacement system with two skeletal replacement linkages.
Figure 6:
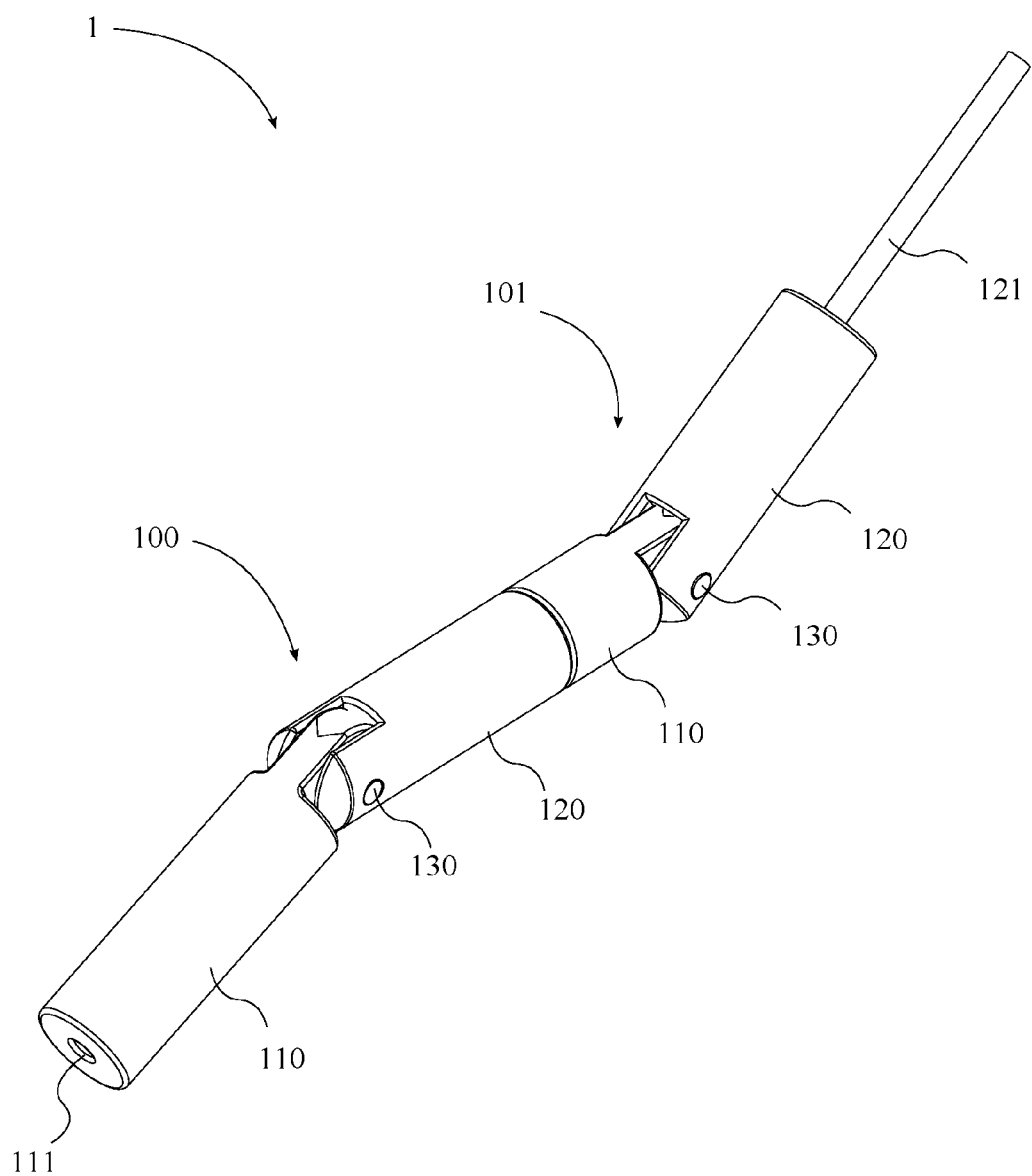
FIG. 6 is a perspective view of another embodiment of the skeletal replacement system with two skeletal replacement linkages.

In some instances, the distance between the hinge 130 of the first skeletal replacement linkage 100 and the hinge 130 of the second skeletal replacement linkage 101 may not be long enough for a particular set of circumstances. For example, a patient with particularly long fingers may need a replacement where the patient's natural DIP joint and PIP joint are further apart than the distance between the hinge 130 of the first skeletal replacement linkage 100 and the hinge 130 of the second skeletal replacement linkage 101, as shown in FIGS. 4-5. In such a case, a spacer can be inserted in between the second member 120 of the first skeletal replacement linkage 100 and the first member 110 of the second skeletal replacement linkage 101. In one embodiment, the space has a cylindrical body with a diameter approximately the same as the diameter of the second member 120 of the first skeletal replacement linkage 100 and/or the first member 110 of the second skeletal replacement linkage 101. The spacer includes a bore 111 at one end that is configured to receive the shaft 121 of the first skeletal replacement linkage 100 and a shaft 121 extending from another end that is configured to be inserted into the bore 111 of the second skeletal replacement linkage 101. In this way the spacer extends the distance between the hinge 130 of the first skeletal replacement linkage 100 and the hinge 130 of the second skeletal replacement linkage 101. In another embodiment, one or more of the second member 120 of the second skeletal replacement linkage 101, the bore 111 end of the spacer, the shaft 121 end of the spacer, or the first member 110 of the second skeletal replacement linkage 101 is trimmed such that the distance between the hinge 130 of the first skeletal replacement linkage 100 and the hinge 130 of the second skeletal replacement linkage 101 is appropriate for insertion into a patient.

The skeletal replacement system 1 can be modified to be used to replace bones and three joints, such as replacing a distal phalange, a DIP joint, a middle phalange, a PIP joint, a proximal phalange, metacarpophalangeal joint, and a portion of a metacarpal bone. The modification of the skeletal replacement system 1 includes adding another skeletal replacement linkage 10 by inserting the shaft 121 of the second skeletal replacement linkage 101 into a bore 111 of a first member 110 of the additional skeletal replacement linkage 10 and inserting a shaft 121 of a second member 120 of the additional skeletal replacement linkage 10 into the metacarpal bone. In this way, the modified version of the skeletal replacement system 1 would include three joints to replace the DIP joint, the PIP joint, and the metacarpophalangeal joint.

In one example, the skeletal replacement system 1 can be used to replace bones and two joints, such as replacing a distal phalanx, a DIP toe joint, a middle phalanx, a PIP toe joint, and a portion of a proximal phalanx in a toe. In the depiction in FIG. 6, the skeletal replacement system 1 is arranged with the hinges 130 at angles that may be natural angles of DIP toe joints and PIP toe joints.

The various embodiments of skeletal replacement linkages 10 and systems described herein can be sized or scaled to replace any bones and/or joints in a patient. For example, a skeletal replacement linkage 10 with two members and a hinge 130 can be scaled to replace portions of a patient's arm bones and elbow. In another example, a skeletal replacement linkage 10 with two members and a hinge 130 can be scaled to replace portions of a patient's leg bones and knee. The various embodiments of skeletal replacement linkages 10 and systems described herein can provide structure for growing or regrowing tissue using stem cell techniques, such as the powder made from pig bladder tissues described above. Such stem cell techniques may not be limited to regrowing tissue for fingers and toes, but may be useful in growing or regrowing tissue in other parts of the body.

Although the invention has been explained in relation to its preferred embodiment, it is to be understood that many other possible modifications and variations can be made without departing from the spirit and scope of the invention as hereinafter claimed.

What is claimed is:

1. A skeletal replacement system comprising:
a first skeletal replacement linkage;
the first skeletal replacement linkage comprising a first member, a second member and a hinge;
the first member of the first skeletal replacement linkage comprising a bore, a first end and a second end opposite to the first end;
the second member of the first skeletal replacement linkage comprising a shaft, a first end and a second end opposite to the first end;
the first member and the second member of the first skeletal replacement linkage being coupled in series with each other;
the bore of the first member of the first skeletal replacement linkage traversing into the first end of the first member of the first skeletal replacement linkage opposite the hinge of the first skeletal replacement linkage;
the shaft of the second member of the first skeletal replacement linkage extending from the second end of the second member of the first skeletal replacement linkage opposite the hinge of the first skeletal replacement linkage;
the second end of the first member and the first end of the second member of the first skeletal replacement linkage being hingedly coupled to each other by the hinge of the first skeletal replacement linkage;
a second skeletal replacement linkage;
the second skeletal replacement linkage comprising a first member, a second member and a hinge;
the first member of the second skeletal replacement linkage comprising a bore, a first end and a second end opposite to the first end;
the second member of the second skeletal replacement linkage comprising a shaft, a first end and a second end opposite to the first end;
the first member and the second member of the second skeletal replacement linkage being coupled in series with each other;

the bore of the first member of the second skeletal replacement linkage traversing into the first end of the first member of the second skeletal replacement linkage opposite the hinge of the second skeletal replacement linkage;

the shaft of the second member of the second skeletal replacement linkage extending from the second end of the second member of the second skeletal replacement linkage opposite the hinge of the second skeletal replacement linkage;

the second end of the first member and the first end of the second member of the second skeletal replacement linkage being hingedly coupled to each other by the hinge of the second skeletal replacement linkage; and the shaft of the second member of one of the first skeletal replacement linkage and the second skeletal replacement linkage being inserted within the bore of the first member of the other of the first skeletal replacement linkage and the second skeletal replacement linkage.

2. The skeletal replacement system as claimed in claim 1 comprising:

the bore of the first member of the first skeletal replacement linkage being concentrically formed on the first end of the first member of the first skeletal replacement linkage;

the shaft of the second member of the first skeletal replacement linkage being concentrically formed on the second end of the second member of the first skeletal replacement linkage;

the bore of the first member of the second skeletal replacement linkage being concentrically formed on the first end of the first member of the second skeletal replacement linkage; and the shaft of the second member of the second skeletal replacement linkage being concentrically formed on the second end of the second member of the second skeletal replacement linkage.

3. The skeletal replacement system as claimed in claim 1 comprising:

the first skeletal replacement linkage and the second skeletal replacement linkage each being configured to replace two bones and a joint in a patient's body.

4. The skeletal replacement system as claimed in claim 1, wherein the first member and the second member of the first skeletal replacement linkage and the first member and the second member of the second skeletal replacement linkage are comprised of non-metallic materials.

5. The skeletal replacement system as claimed in claim 4, wherein the non-metallic materials comprise one or more of medical grade plastic or medical grade ceramic.

6. The skeletal replacement system as claimed in claim 1 comprising:

the shaft of the second member of the one of the first skeletal replacement linkage and the second skeletal replacement linkage being adhered to the bore of the first member of the other of the first skeletal replacement linkage and the second skeletal replacement linkage.

7. The skeletal replacement system as claimed in claim 1 comprising:

the shaft of the second member of the one of the first skeletal replacement linkage and the second skeletal replacement linkage being press fit into the bore of the first member of the other of the first skeletal replacement linkage and the second skeletal replacement linkage.

8. The skeletal replacement system as claimed in claim 1, wherein the first skeletal replacement linkage and the second skeletal replacement linkage are configured to replace a first bone, a second bone, a third bone, a first joint between the first and second bones and a second joint between the second and third bones in a patient's body.

9. A method of treating a patient by using the skeletal replacement system of claim 1, the method comprising the steps of:

preparing a first bone of a patient to receive the shaft of the second member of the one of the first skeletal replacement linkage and the second skeletal replacement linkage;

trimming the second member of the one of the first skeletal replacement linkage and the second skeletal replacement linkage based on an intended distance from the prepared first bone to an intended location of the hinge of the one of the first skeletal replacement linkage and the second skeletal replacement linkage;

inserting the shaft of the second member of the one of the first skeletal replacement linkage and the second skeletal replacement linkage into the prepared first bone; and placing tissue around the one of the first skeletal replacement linkage and the second skeletal replacement linkage.

10. The method of claim 9 comprising the step of:

removing a second bone, a joint between the second bone and the first bone and a portion of the first bone from the patient, wherein the first member, the hinge and the second member of the one of the first skeletal replacement linkage and the second skeletal replacement linkage are configured to replace the second bone, the joint and the portion of the first bone.

11. The method of claim 9 comprising the step of:

placing tissue around the one of the first skeletal replacement linkage and the second skeletal replacement linkage by replacing the patient's tissue around the one of the first skeletal replacement linkage and the second skeletal replacement linkage.

12. The method of claim 9 comprising the step of:

placing tissue around the one of the first skeletal replacement linkage and the second skeletal replacement linkage by regrowing the tissue around the one of the first skeletal replacement linkage and the second skeletal replacement linkage using a stem cell technique.

13. The method of claim 9 comprising the step of:

placing tissue around the one of the first skeletal replacement linkage and the second skeletal replacement linkage by growing the tissue around the one of the first skeletal replacement linkage and the second skeletal replacement linkage before inserting the shaft of the second member of the one of the first skeletal replacement linkage and the second skeletal replacement linkage into the prepared first bone.

* * * * *